United States Patent [19]

Smith

[11] Patent Number: 4,583,293

[45] Date of Patent: Apr. 22, 1986

[54] LIQUID LEVEL GAUGE AND SAMPLING DEVICE

[76] Inventor: Wanda L. Smith, 1247 Petit Ave., #461, Ventura, Calif. 93004

[21] Appl. No.: 605,307

[22] Filed: Apr. 30, 1984

[51] Int. Cl.$^4$ .......................... G01F 23/04; G01B 5/18
[52] U.S. Cl. .................................. 33/126.4 R; 73/291; 73/298; 73/864.63
[58] Field of Search ................ 73/298, 864.63, 864.65; 33/126.4 R; 137/558; 116/227

[56] References Cited

U.S. PATENT DOCUMENTS

| | | | |
|---|---|---|---|
| 568,572 | 9/1896 | Hewson | 137/614.05 |
| 1,039,923 | 10/1912 | Ganey | 73/864.63 |
| 1,845,709 | 2/1932 | Haddon | 73/864.63 |
| 2,751,787 | 6/1956 | Porter | 73/298 |
| 2,985,180 | 5/1961 | Grayson | 137/74 |
| 3,371,538 | 3/1968 | Bagby | 73/864.65 |
| 4,335,606 | 6/1982 | Michalak | 73/298 |
| 4,440,193 | 4/1984 | Matheson | 137/558 |

FOREIGN PATENT DOCUMENTS 0034616 10/1908 Austria .

Primary Examiner—Charles Frankfort
Assistant Examiner—Thomas B. Will
Attorney, Agent, or Firm—Jack C. Munro

[57] ABSTRACT

A liquid level determining and sampling device which takes the form of a transparent elongated tubular member which has a sealing plug attached at the lower end thereof. Fluid conducting openings are located about the sealing plug to permit liquid to be conducted past the sealing plug to within the tubular member. A sleeve is threadably engaged to the lower end of the tubular member. The sleeve interiorly includes a sealing plate within which is formed a hole. The sleeve is to be movable with respect to the tubular member so the sealing plug can either be spaced from the hole or tightly engaged with the wall of the hole. Fluid conducting openings are formed through the side wall of the sleeve adjacent the outer end thereof to permit liquid to be conducted through the hole, through the fluid and into the tubular member. The outer end of the sleeve includes a resilient ring which is to frictionally engage with the bottom of the tank which contains liquid the level of which is to be measured. The resilient ring is to hold the sleeve motionless within the tubular member as it is rotated relative to the sleeve.

5 Claims, 4 Drawing Figures

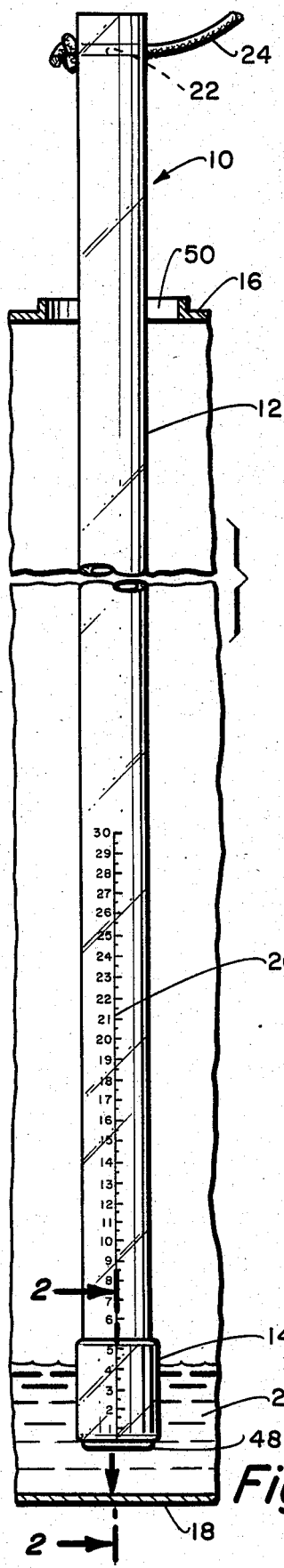
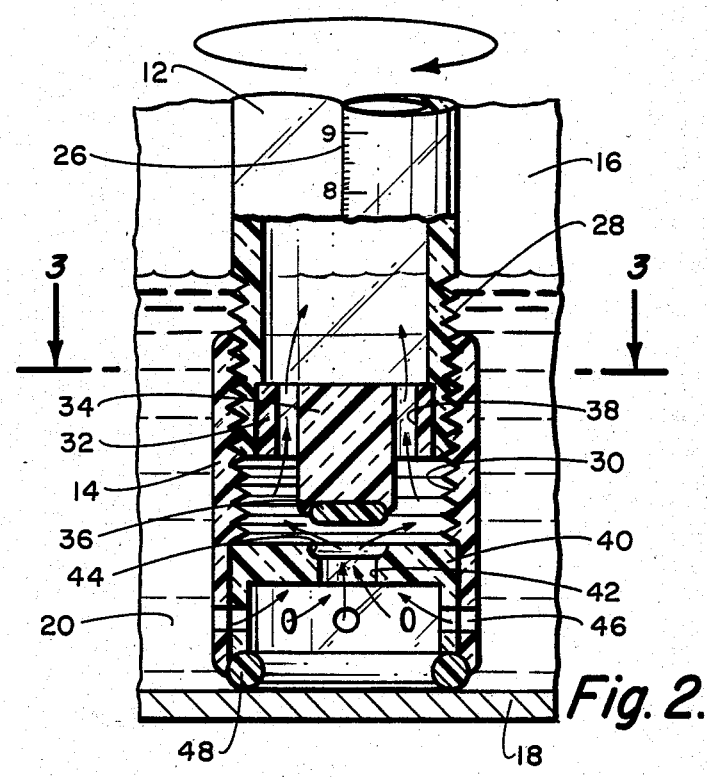
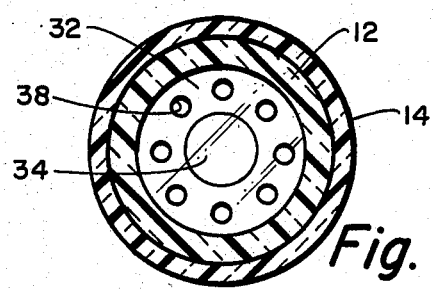
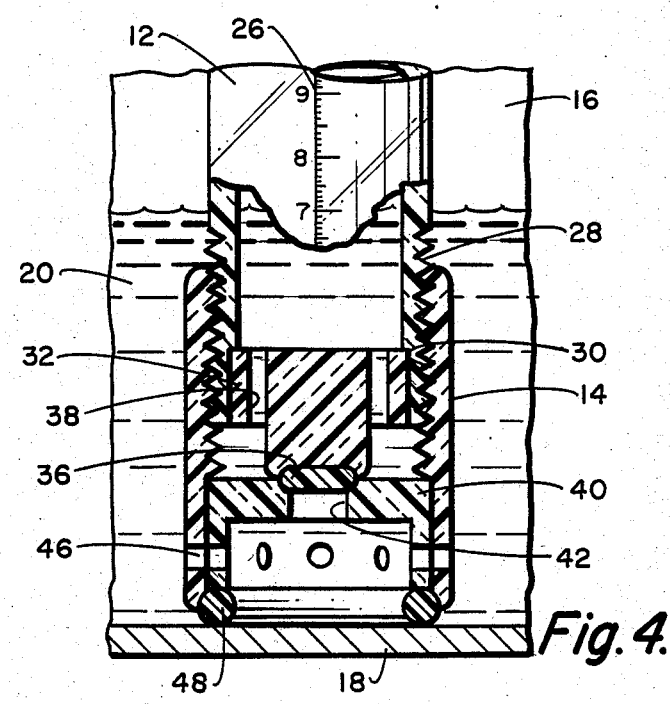

LIQUID LEVEL GAUGE AND SAMPLING DEVICE

BACKGROUND OF THE INVENTION

The field of this invention relates to a liquid level gauge and sampling device and more particularly to a liquid level gauge and sampling device of the type comprising a tube which is to be lowered into a reservoir, permitting the liquid to rise within the tube to the level of the liquid in the reservoir, closing the tube to prevent escape of liquid therefrom, and then withdrawing of the tube from the reservoir to determine the level of the liquid (or liquids) in the reservoir by observing the level of the liquid in the tube.

At times it is desirable to determine the quantity of liquid within a tank. For the most part, it is usually very difficult to determine the level of the liquid in a tank. Frequently, such tanks are buried in the ground or are so large that the level of liquid cannot be easily determined. A further complication is that frequently such tanks are cylindrical and are positioned on the side. Mathematically it is difficult to determine the quantity of liquid in such a tank.

A common usage of such tanks is in gasoline service stations. Usually tank measurements are taken at the end of each day and are recorded and corresponded to the amount of gasoline which is pumped each day. The normal prior art method of measuring the liquid in the tank is to use a wooden measuring stick which includes a measurement scale on the side thereof. However, at times it is difficult to accurately read the measuring stick, since the operator must look for the line between the wet and dry area of the stick. This is sometimes very difficult to determine especially if it is night time.

Additionally, it must be determined if there is any water in the tank. Water is heavier than gasoline and therefore will settle to the bottom of the tank. If it is known that the water in the tank has risen to an undesirable level, it can be removed.

SUMMARY OF THE INVENTION

The structure of this invention relates to a device which is to facilitate the accurate determining of the level of liquid in a tank and also the type or types of liquid located in the tank. Further, the device of this invention facilitates ascertaining the levels of these different types of liquids in a tank, if there are different types of liquids in a tank. Further, the device of this invention can be used to remove the heaviest liquid in the tank.

The device of this invention includes an elongated transparent tubular member which will normally include on the side thereof a measuring scale. At the lower or bottom end of the tubular member and located substantially along the longitudinal center axis of the tubular member is a sealing plug. Located about the sealing plug is an opening assembly which connects within the interior of the tubular member. The exterior section of the tubular member located about the sealing plug is threaded. A sleeve is threadably engaged with this exterior threaded section of the tubular member. Interiorly of the sleeve there is located thereacross a sealing plate. Centrally disposed within the sealing plate is a hole. The sleeve can be moved relative to the tubular members so that the hole is closed by the sealing plug. Alongside the sealing plug are a series of openings. A resilient sealing ring is attached to the outermost or free end of the sleeve. This ring is to engage with the bottom of a tank and is to then be held motionless due to the frictional engagement between the ring and the tank. The tubular member can then be freely rotated due to the threaded connection relative to the sleeve. Therefore, the tubular member can be rotated to permit liquid to be conducted into the tubular member and then rotated to close the hole and prevent escape of liquid from the tubular member. The tubular member can then be withdrawn and the level of the liquid within the tubular member determined, as well as the type of liquid.

BRIEF DESCRIPTION OF THE DRAWING

FIG. 1 is a side elevational view of the liquid level determining and sampling device of this invention showing its location within a tank which contains liquid to be measured;

FIG. 2 is a cross-sectional view of the bottom portion of the device of this invention showing the tubular member in the position to permit entry of the liquid therewithin;

FIG. 3 is a cross-sectional view taken along line 3—3 of FIG. 2; and

FIG. 4 is a cross-sectional view similar to FIG. 2 but showing the device in the closed position not permitting entry of liquid into the tubular member.

DETAILED DESCRIPTION OF THE SHOWN EMBODIMENT

Referring particularly to the drawing, there is shown the liquid level determining and sampling device 10 of this invention which is composed generally of a tubular member 12 and a sleeve 14. Device 10 is adapted to be located within a tank 16 which has a bottom wall 18. Within the tank 16 is located a quantity of liquid 20.

The tubular member 10 at its outer end thereof has a hole 22. Through the hole 22 is to be located a section of rope or string 24. The reason for the rope or string 24 is if the device 10 of this invention is located entirely within the confines of the tank 16, and the device 10 is accidentally released from the grasp of the user, that the rope or string 24 will prevent loosing of the device 10.

The elongated tubular member 12 is to be constructed of transparent material such as plastic. On the exterior sidewall of the tubular member 12 there is inscribed a measuring scale 26. This measuring scale can be in any desired measurement and generally will be in centimeters or inches. The measurement scale 26 is inscribed on the elongated tubular member 12 when the device 10 of this invention is in the closed position shown in FIG. 4 of the drawing.

The lower end of the tubular member 12 contains a series of external screw threads 28. The screw threads 28 are threadably engaged with a series of internal threads 30 formed within the sleeve 14. Free rotational movement between the tubular member 12 and the sleeve 14 through the interaction between the threads 28 and 30. It is to be understood that rotational movement of the tubular member 12 relative to the sleeve 14 results in lineal movement therebetween.

Located within the interior of the tubular member 12 at the bottom thereof is a disc 32. A tight engagement between the interior wall of the tubular member 12 and the disc 32 is established.

Centrally attached to the disc 32 and protruding outwardly therefrom is a sealing plug 34. Attached to the outer end of the sealing plug 34 is a first sealing ring 36.

Located about sealing plug 34 and formed within the disc 32 are a series of first openings 38. There are actually eight in number of first openings 38. It is considered to be within the scope of this invention that any desirable number of such openings could be employed. The sealing plug 36 will normally take the form of a rubber or plastic which should be readily deflectable something equivalent to an O-ring type of seal.

Attached within the outer or free end of the sleeve 14 is a sealing plate 40. The sealing plate 40 has a centrally located hole 42. The inner end of hole 42 connects with an enlarged annular sealing seat 44. This sealing plug 36 is to be capable of engagement with the sealing seat 44 thereby closing of the hole 40. This is shown in FIG. 4.

Formed through the sidewall of the sleeve 14 adjacent its outer or free end are a series of second openings 46. The outermost or free end of the sleeve 14 has attached thereto a sealing ring 48. The material of construction of the sealing ring 48 will normally comprise a resilient rubber or plastic.

The operator can utilize the apparatus of this invention in two different ways. The first way is to move the tubular member 12 relative to the sleeve 14 so as to close the hole 42, as is shown in FIG. 4 of the drawing. The operator then inserts the tubular member 12 through the access opening 50 of the tank 16 until the sealing ring 48 is frictionally engaged with the bottom 18. The operator then rotates the tubular member 12 one half to one turn relative to the sleeve 14. This causes the sealing member 26 to be disengaged from the seat 44 and be spaced therefrom. As a result, liquid is conductable from directly adjacent the bottom of the tank 18 through the openings 46, through hole 42, through openings 38 to seek its own level in the tubular member 12. This occurs within a matter of a second or two. The operator then rotates the tubular member 12 to seal tightly the sealing member 36 with the seat 44. This closes the hole 42. The operator is to then remove the device 10 out of the interior of the tank 16 and by observing of the level of liquid within the tubular member 12 and by the measuring scale 26 one can determine the quantity of liquid within the tank 16. Also, since the liquid was taken right from the bottom of the tank 18, it can be readily ascertained exactly what type of liquid is at the bottom of the tank. In other words, if the liquid is mostly water, then the user is informed that there is water in the bottom of the tank. If the liquid is gasoline, then the user knows that there is no water in the tank 16.

The other way that the device 10 of this invention is to be used is by inserting the device 10 into the tank 16 with the sealing member 36 unseated from the seat 44. Therefore, as the device is inserted, liquid is caused to occupy the tubular member 12 and upon the sealing ring 48 coming into contact with the bottom 18 of the tank and the operator rotating the tubular member 12 relative to the sleeve 14 to seat the sealing member 36 within the seat 44, the operator can then remove the device 10 in the normal manner. The same level of liquid should be indicated as in the first method of operation, but if there is water in the bottom of the tank, the level of the water in the tubular member 12 should be representative of the level of the water within the tank. In this way, it can be determined whether it is necessary to remove the water if the level is more than desired.

It is to be reiterated that device 10 can be used to remove water from the bottom of the tank. The accumulated water would of course be discarded. There is no known device within the prior art which achieves this function.

With the device located on the bottom of the tank, there may be some silt which makes it difficult to open the valve 36 with the ring 48 slipping. It is anticipated that this will not occur in most instances. However, if this problem does occur, the user may modify the ring 48 to include some form of small projections, such as small nail-like spikes. These spikes would penetrate through the silt and establish a firm contact at the bottom of the tank.

What is claimed is:

1. A liquid level determining and sampling device comprising:

an elongated tubular member having a lower end and an upper end, said lower end including a series of exterior screw threads, a sealing plug secured within said tubular member, a first opening assembly mounted about said sealing plug, liquid is to be able to be conducted through said first opening assembly into the interior of said tubular member;

a sleeve having a lower end and an upper end, said upper end connected to said exterior screw threads, within and across said sleeve there is mounted a sealing plate, said sealing plate having a hole, said tubular member being movable relative to said sleeve between a lower position and an upper position, said lower position being when said sealing plug closes said hole, said upper position being when said sealing plug is spaced from said hole permitting passage of liquid through said hole and said first opening assembly into said tubular member; and a second opening assembly formed through the side wall of said sleeve, said second opening assembly connecting with said hole, whereby said lower end of said sleeve is to be positioned against and frictionally engaged with the bottom of a tank of liquid and with said tubular member in said upper position liquid is permitted to be conducted within said tubular member to obtain its own level, and the operator can then rotate said tubular member relative to said sleeve which is frictionally engaged with the bottom of the tank which results in said tubular member being located in said lower position thereby confining the liquid within said tubular member, said tubular member to be withdrawin form said tank to thereby determine the level of liquid within the tank and also the type of liquid.

2. The liquid level determining and sampling device as defined in claim 1 wherein:

said tubular member being transparent to thereby easily observe the liquid therewithin.

3. The liquid level determining and sampling device as claimed in claim 2 wherein:

indicia being located on the exterior of said tubular member to facilitate the accurate measurement of the quantity of liquid being contained within the tubular member and thereby the tank.

4. The liquid level determining and sampling device as defined in claim 3 wherein:

said sealing plug including a resilient sealing member, said resilient sealing member to engage with said hole.

5. The liquid level determining and sampling device as claimed in claim 4 wherein:

said lower end of said sleeve including a second resilient sealing ring, said second resilient sealing ring to frictionally engage with the bottom of the tank to thereby hold said sleeve motionless during rotation of said tubular member.

* * * * *